United States Patent [19]

Tittel

[11] Patent Number: 4,465,482
[45] Date of Patent: Aug. 14, 1984

[54] SUCTION DRAINAGE TUBE

[75] Inventor: Klaus Tittel, Mainz, Fed. Rep. of Germany

[73] Assignee: Gerhard Hug GmbH, Umkirch, Fed. Rep. of Germany

[21] Appl. No.: 564,765

[22] Filed: Dec. 28, 1983

Related U.S. Application Data

[63] Continuation of Ser. No. 389,255, Jun. 17, 1982, abandoned, which is a continuation of Ser. No. 127,762, Mar. 6, 1980, abandoned.

[30] Foreign Application Priority Data

Mar. 6, 1980 [DE] Fed. Rep. of Germany ....... 2908952

[51] Int. Cl.³ ............................................ A61M 25/00
[52] U.S. Cl. ..................................... 604/280; 128/343
[58] Field of Search ................ D24/54, 59; 128/348, 128/349 R, 350 R, 350 V, 343; 119/14.19, 14.20, 14.21; 604/93, 264, 280, 281 (U.S. only), 286, 369, 266, 268, 43, 45, 283, 284, 95, 105; 138/129, 103, 154

[56] References Cited

U.S. PATENT DOCUMENTS

| D. 33,456 | 10/1900 | Harris | D24/54 |
|---|---|---|---|
| 572,713 | 12/1896 | O'Sullivan | 119/14.21 |
| 1,719,428 | 7/1929 | Friedman | 604/105 |
| 1,888,349 | 11/1932 | Jacoby | 128/349 R |
| 3,108,595 | 10/1963 | Overment | 604/105 |
| 3,621,848 | 11/1971 | Mcgovern | 128/350 R |
| 3,815,608 | 6/1974 | Spinoza | 128/350 R |
| 3,946,741 | 3/1976 | Adair | 504/105 |
| 4,276,874 | 7/1981 | Wolvek et al. | 128/1 D |

FOREIGN PATENT DOCUMENTS

| 2007788 | 10/1970 | Fed. Rep. of Germany. |
| 2528273 | 10/1976 | Fed. Rep. of Germany. |
| 484679 | 3/1970 | Switzerland. |
| 531886 | 2/1973 | Switzerland. |
| 955490 | 4/1964 | United Kingdom ............ 604/105 |

OTHER PUBLICATIONS

"Catheter", Webster's New Collegiate Dictionary, G & C Merriam Co. Springfield, Mass., 1973.

Primary Examiner—C. Fred Rosenbaum
Assistant Examiner—J. L. Kruter
Attorney, Agent, or Firm—Frishauf, Holtz, Goodman & Woodward

[57] ABSTRACT

Perforations at the insertion end portion of a suction drainage tube for draining body fluids are of a shape bounded on at least two opposite sides by the edges of helical land portions of the tubing wall. One or more helical slots or a pattern of diamond-shaped openings may accordingly be provided. Twisting the tube after its insertion can be done to dislodge obstructions that may build up. In withdrawing the tube, the diameter tends to be reduced, thus facilitating removal.

5 Claims, 4 Drawing Figures

SUCTION DRAINAGE TUBE

This is a continuation of application Ser. No. 389,255, filed on June 17, 1982, now abandoned, which is a continuation of Ser. No. 127,762 filed Mar. 6, 1980, now abandoned.

This invention relates to a suction drainage tube for medical purposes, consisting of a tube and a number of perforations in the region of the tube end which is intended to be implanted in a living body.

Suction drainage tubes are generally made of polyvinyl chloride with an outside diameter of about 2.5 to 5 mm and a length of about 2 meter. The end portion of the tube, as presently known, is usually provided with transverse bores of a diameter of about 2 mm. After the perforated end has been shortened to a suitable length, these suction drainage tubes are implanted into body and tissue cavities from which tissue fluid is to be drained. The suction applied is about 60 to 90 mm Hg, i.e. 8 to 12 kPa. This suction causes body cavity tissue to be drawn against the wall of the suction drainage tube. After implantation, the amount of tissue fluid discharged fluctuates considerably and there are times when there is practically no discharge of tissue fluid whatever. During such times the tissue fluid coagulates more intensively, and clogs not only a number of the perforations, but also the interior of the tube. If the tissue fluid discharge then increases subsequently, it cannot be drawn off properly.

The object of the invention is to provide a suction drainage tube with a reduced risk of obstruction and with which any obstruction occurring can be readily cleared.

SUMMARY OF THE INVENTION

Briefly, the perforations of the insertion-end portion of the suction drainage tube are formed between helical lands of the tube wall.

In one embodiment of the invention, a single helical land is provided, between the individual helical turns of which a helical slot is formed as a single elongated perforation. If the implanted tube is twisted slightly from outside the implanted portion, the tube wall is fully rotated as a result, but the helical turns are rotated only partially. Depending upon the direction in which the tube is twisted, the helical slot will be widened or constricted, and there will in every case be a relative displacement of the edges of the helical slot. Any coagulation is thus opened. Another advantage of the helical slot is that the interior of the tube does not just have a round cross-section near the tube end, but is more in the form of a keyhole. With this cross-section the adhesion forces occurring cannot take effect in the same way as with a purely round cross-section. There is therefore less coalescence from the outset.

In a second embodiment of the invention, two intersecting helical lands are provided, between which diamond-shaped perforations are formed. In this embodiment, the perforations may make up about 50% of the tube wall area. The proportion of lateral openings in this embodiment is particularly great, so that there is little risk of obstruction. The edges of the perforations can be moved relatively to one another by pulling and turning, although not to the same extent as in the first embodiment of the invention. The perforated end portion of the tube can be cut to any desired length without making insertion more difficult.

BRIEF DESCRIPTION OF THE DRAWINGS

Further details of the invention will be explained by way of example in the following description of two particular embodiments with reference to the annexed drawing, wherein.

DESCRIPTION OF THE PREFERRED EMBODIMENTS

Figure 1:
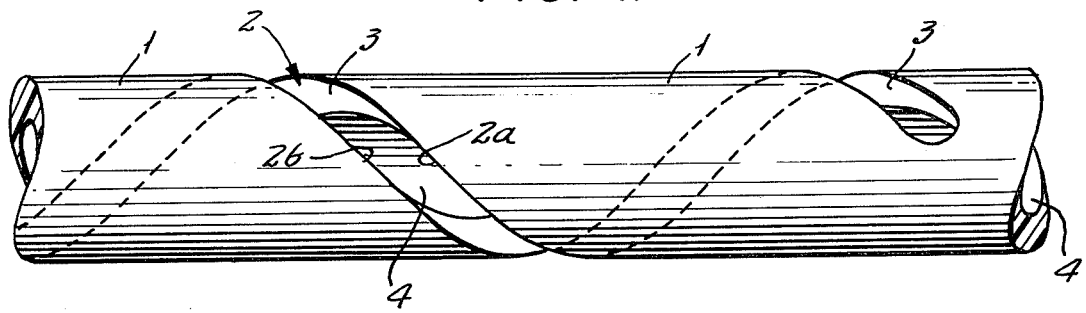
FIG. 1 is an enlarged-scale side view of the transition between the slotted and solid portion of a suction drainage tube according to the first embodiment.
Figure 3:
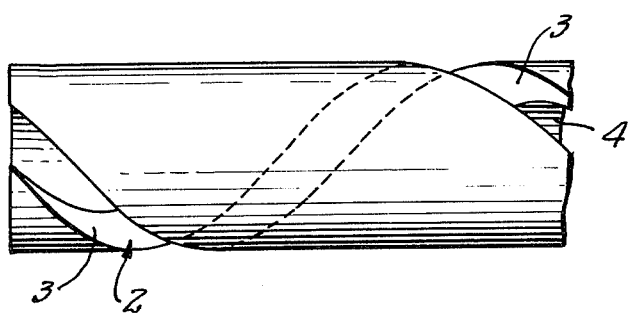
FIGS. 3 and 4 are side views of the perspective free ends of the perforated portions of the tubes illustrated in FIGS. 1 and 2.

FIG. 1 is an enlarged-scale view of the transition portion of a first embodiment of a suction drainage tube according to the invention. The drainage tube, of which only a portion is shown, consists of a length of tubing of about 1 meter, made from polyvinyl chloride or some other suitable plastic, and has an outside diameter of about 2.5 to 5 mm. The perforated end of the tube is about 15 to 20 cm long and has a spiral slot 2 which has some 8 to 10 helical turns, one of which is shown. The remaining 80 to 85 cm of the tube extend to the right in FIG. 1 beyond the place where the tube is shown broken off, this extension being usually a simple solidwall tube. The helical slot 2 divides the wall of the tube so as to form a single helical land 1, the edge surfaces of which are visible at 3. Although the tube interior 4 is cylindrical, it extends out through the helical slot 2, so that any cross-section gives an approximately keyhole-shape, the length of the "bit" of which is shortened however. The helical slot 2 occupies some 25% of the wall area of the slotted portion of the tubing. The free end of the slotted portion of the tube is shown in FIG. 3. It is not necessary to close the slot at the tube end.

If an external twisting force is applied to the tube, a shearing force occurs in the land 1 and cannot be transmitted in the region of the slot 2. Consequently, the slot edges 2a, 2b move towards or away from one another depending upon the direction of rotation of the tube. Any obstruction occurring during implantation is thus cleared so that flow into the tube through the slot and through the tube interior 4 is again assured.

Figure 2:
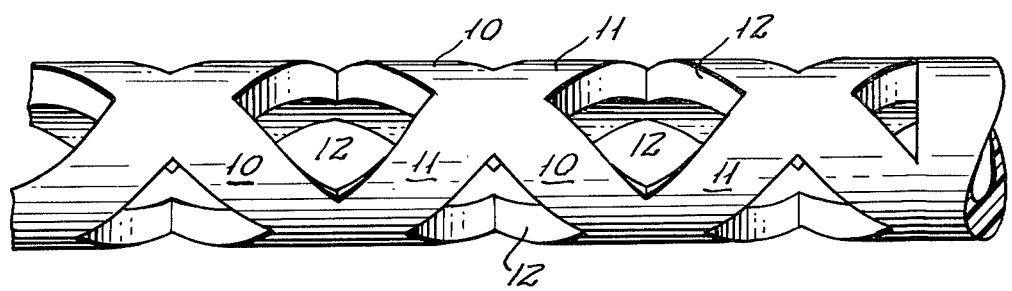
FIG. 2 shows, also in side view, the corresponding portion of a suction drainage tube according to the second embodiment.

FIG. 2 shows another embodiment of a suction drainage tube, again in the form of a portion at the transition between the perforated end and the remaining part of the tube. Diamond-shaped perforations 12 are provided and extend along helical boundary lines, but leave lands 10 and 11 free as two intersecting helical strips. Since a perforated tube end of this kind is relatively flexible and deformable, the shape of the perforations 12 can be altered by pulling or turning the tube, so that it is possible to open up any coalescence. Moreover, the risk of any obstruction occurring is reduced from the outset, because of the considerable number of breaks in the tube wall. Another important feature is that when the suction drainage tube is removed, the diameter of the perforated ennd is slightly reduced so that this end of the tube can readily be withdrawn from the wound.

Figure 4:
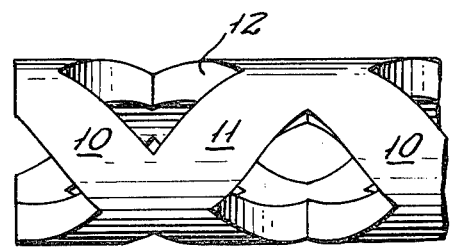

The tube partly illustrated in FIG. 2 may, for example, have the free end of its perforated portion as shown in FIG. 4. The length of the perforated portion can be trimmed to any desired value before use.

Although the invention has been described by reference to two specific illustrated embodiments, it will be understood that variations and modifications are possible with in the inventive concept. For example, a variant of the first embodiment could be made with two diametrically opposed helical slots instead of a single helical slot. More than two such slots are also possible. In general, the more slots that are used, the greater the pitch of the helical slot edges should be. Similarly, variants of the second embodiment with more than two helical land strips are possible, and the strips winding in one direction can differ in number and/or in helix pitch from those winding in the other direction.

We claim:

1. A suction drainage tube having a distal and proximal end means for implantation into a living body and for connection to a suction device for medical purposes, said tube consisting of a length of flexible tubing having a substantially cylindrical wall made of a single constant thickness of plastic tubing and said distal end portion provided with at least one substantially helically shaped open means slot passing completely through said cylindrical wall at said distal end running for the complete length of said distal end portion and terminating with said open slot means end at the tip of said portion of said tubing wall, said slot means having a constant width, in the unstressed condition of drainage tube, substantially less than the width of the helical land strip constituted by the slotted end portion means and having distal end means of said tubing wall and capable of having its width changed and its edges relatively shifted by partial rotation for clearing helical slot obstructions by a twisting force applied at or near the proximate end of said tube remote from the slotted end portion when the tube is implanted in a living body.

2. A suction drainage tube as defined in claim 1, made of tubing of an outside diameter between 2.5 and 5 mm, in which said cylindrical tubing wall end portion has a single helically shaped slot.

3. A suction drainage tube as defined in claim 2, in which said helical slot, in the unstressed condition of said drainage tube, is between 0.8 and 2.5 mm wide and the helical land strip constituted by the slotted end portion of said tubing wall is between 8 and 10 mm wide.

4. A suction drainage tube as defined in claim 2 or 3 in which said slot has a length of between 2 and 15 mm.

5. A suction drainage tube as defined in claim 4, in which said slot has a length of between 10 and 15 mm.

* * * * *

UNITED STATES PATENT AND TRADEMARK OFFICE
CERTIFICATE OF CORRECTION

PATENT NO. : 4,465,482
DATED : August 14, 1984
INVENTOR(S) : Klaus TITEL et al

It is certified that error appears in the above-identified patent and that said Letters Patent is hereby corrected as shown below:

Priority date should be -- Mar. 7, 1979 --

Claim 11, col. 3, line 22, after "open" delete "means" and after "slot" insert -- means --.

Claim 11, col. 4, lines 4 & 5 delete "and having distal end means";

Claim 11, col. 4, line 5, after "tubing wall and" insert -- having distal end means --;

Claim 11, col. 4, line 8, "proximate" should be -- proximal --.

Signed and Sealed this

Twenty-fourth Day of December 1985

[SEAL]

Attest:

DONALD J. QUIGG

Attesting Officer

Commissioner of Patents and Trademarks